United States Patent [19]
Xu et al.

[11] Patent Number: 5,885,818
[45] Date of Patent: Mar. 23, 1999

[54] **METHOD FOR CLONING AND PRODUCING AGEI RESTRICTION ENDONUCLEASE IN *E. COLI***

[75] Inventors: Shuang-yong Xu, Lexington; Robert E. Maunus, Danvers; Keith D. Lunnen, Essex; Rachel Allen, Beverly, all of Mass.

[73] Assignee: New England Biolabs, Inc., Beverly, Mass.

[21] Appl. No.: 78,459

[22] Filed: May 14, 1998

[51] Int. Cl.$^6$ .............................. C12N 9/16; C12N 15/55
[52] U.S. Cl. ................ 435/196; 435/320.1; 435/252.3; 435/325; 435/419; 536/23.2
[58] Field of Search ...................... 435/196, 320.1, 435/252.3, 325, 419; 536/23.2

[56] References Cited

U.S. PATENT DOCUMENTS

| | | | |
|---|---|---|---|
| 5,200,333 | 4/1993 | Wilson | 435/172.3 |
| 5,498,535 | 3/1996 | Fomenkov | 435/172.3 |
| 5,721,126 | 2/1998 | Xu | 435/199 |

OTHER PUBLICATIONS

Blumenthal, et al. J. Bacter., 164:501–509 (1985).
Bougueleret, et al., Nucl. Acids. Res., 12:3659–3676 (1984).
Yamada, et al., Agric. Biol. Chem., 53:1747–1749 (1989).
Mizuno, et al., Agric. Biol. Chem., 54:1797–1802 (1990).
Fomenkov, et al. Nucl. Acids Res. 22:2399–2403 (1994).
Gingeras and Brooks, Proc. Natl. Acad. Sci. USA 80:402–406 (1983).
Suzuki, et al., Biosci. Biotech. Biochem., 60:444–447 (1996).
Kiss, et al. Nucl. Acids Res. 13:6403–6419 (1985).
Kosykh, et al. Molec. Gen. Genet., 178:717–718 (1980).
Walder, et al., J. Biol. Chem., 258:1235–1241 (1983).
Mann, et al., Gene, 3:97–112 (1978).
Roberts and Macelis, Nucl. Acids Res. 25:248–262 (1997).
Theriault and Roy, Gene, 19:355–359 (1982).
Walder, et al., Proc. Natl. Acad. Sci. USA, 78:1503–1507 (1981).
Szomolanyi, et al., Gene 10:219–225 (1980).
Janulaitis, et al., Gene, 20:197–204 (1982).
Kiss and Baldauf, Gene, 21:111–119 (1983).

*Primary Examiner*—Keith D. Hendricks
*Attorney, Agent, or Firm*—Gregory D. Williams

[57] ABSTRACT

The present invention relates to recombinant DNA which encodes the AgeI restriction endonuclease as well as AgeI methyltransferase, and production of AgeI restriction endonuclease from *E. coli* cells containing the recombinant DNA.

6 Claims, 4 Drawing Sheets

FIG. 1

FIG. 2

```
  1 ATGGGGCCATCAACGCTGAAAAGGAGAAAACCAATGACCAAAACCACCTATATCGCCACC
    ----------+---------+---------+---------+---------+---------+
    M  G  P  S  T  L  K  R  R  K  P  M  T  K  T  T  Y  I  A  T
 61 GCACCTGATGGATCGGAACTCACTCGCAAGACCGACCGAACCTACACCCACGCGGTCTTG
    ----------+---------+---------+---------+---------+---------+
     A  P  D  G  S  E  L  T  R  K  T  D  R  T  Y  T  H  A  V  L
121 TTAGAGGGCAAGGAGGGCTGGAAAGCTGAGGGGTTCTFCGGACGTCTCGACCTFFCCCAC
    ----------+---------+---------+---------+---------+---------+
     L  E  G  K  E  G  W  K  A  E  G  F  C  G  R  L  D  L  A  H
181 AAGAAGCAACTTGAGCATCCTGGCAGTATCGTCGTGGAAGTCAAAGCGCTCGGTGACGCA
    ----------+---------+---------+---------+---------+---------+
     K  K  Q  L  E  H  P  G  S  I  V  V  E  V  K  A  L  G  D  A
241 CAGACCGACAAGCCTAAGGCCGAAGCTACCGAAGACGCTGAACCGACCAAAGATGAGACG
    ----------+---------+---------+---------+---------+---------+
     Q  T  D  K  P  K  A  E  A  T  E  D  A  E  P  T  K  D  E  T
301 GTTGGACGCCCCGAAGAAGAGCCGAGCGTCGATGAGAAAATCAGGAACGCAAAGGTTACA
    ----------+---------+---------+---------+---------+---------+
     V  G  R  P  E  E  E  P  S  V  D  E  K  I  R  N  A  K  V  T
361 GGTCCCGAGCGCAAGGGCAAAATCGGAGACCTTGTGCACGAGTTGTTGATGGACGAGACG
    ----------+---------+---------+---------+---------+---------+
     G  P  E  R  K  G  K  I  G  D  L  V  H  E  L  L  M  D  E  T
421 TTGGATTATGTGACGATCGTGGATCGGGTCATGGCAAATTTCCTGATGCCAAAACCACGG
    ----------+---------+---------+---------+---------+---------+
     L  D  Y  V  T  I  V  D  R  V  M  A  N  F  L  M  P  K  P  R
481 CACGTTCAGTCGCATCTGTGGCGGCTGTTCTCCGCAAGAAGGGTGCTGAAGTACCCAAAC
    ----------+---------+---------+---------+---------+---------+
     H  V  Q  S  H  L  W  R  L  F  S  A  R  R  V  L  K  Y  P  N
541 GCCGGAAATCCAAGGTATGACCTCATGCGGGCAACTTGCCGAAAGGGGCGTTGTCACTGG
    ----------+---------+---------+---------+---------+---------+
     A  G  N  P  R  Y  D  L  M  R  A  T  C  R  K  G  R  C  H  W
601 TCTAGTGGCGACGTCCTCAATATATTTGGCGTTCCGTTGGTCATTCATACCCGATATGGT
    ----------+---------+---------+---------+---------+---------+
     S  S  G  D  V  L  N  I  F  G  V  P  L  V  I  H  T  R  Y  G
661 GTCTGCAAATATCCTCGCTGA 681
    ----------+---------+-
     V  C  K  Y  P  R  *
```

FIG. 3

```
   1 ATGAAGACGATCGATCTATTTTGCGGGGCTGGAGGATTAGGAGAAGGCTTTAGACAGGCA
     M  K  T  I  D  L  F  C  G  A  G  G  L  G  E  G  F  R  Q  A
  61 GGATTTTCAGCGCTGTACGCCAATGACCATGAGACCCCTGCGCTTGCAACATACAAGGAA
     G  F  S  A  L  Y  A  N  D  H  E  T  P  A  L  A  T  Y  K  E
 121 AACCATCCAGACGCAGTATGCTCGACTGATTCCATCGAGACTGTAGACCCCAAGAAAATT
     N  H  P  D  A  V  C  S  T  D  S  I  E  T  V  D  P  K  K  I
 181 CGCGAAGACCTTGGCGTCGCGCCTGGACAGGTTGACGTGGTTATGGGGGGGCCTCCCTGT
     R  E  D  L  G  V  A  P  G  Q  V  D  V  V  M  G  G  P  P  C
 241 CAAGGCTTCTCAACCTACGGGCAGCGACGCGACGACGATGCGAGGAACCAACTGTACGTC
     Q  G  F  S  T  Y  G  Q  R  R  D  D  D  A  R  N  Q  L  Y  V
 301 CCGTATTTCGGTTTCGTTGAAGAGTTCCGACCTAAGGCATTTCTGATCGAGAACGTGGTC
     P  Y  F  G  F  V  E  E  F  R  P  K  A  F  L  I  E  N  V  V
 361 GGGTTGCTCTCAATGTCTGGAGGCGCGGTACTTGCAGACATGGTCGCCCGCGCAGAGGCA
     G  L  L  S  M  S  G  G  A  V  L  A  D  M  V  A  R  A  E  A
 421 CTCGGTTATGCTGCTGACGTGGTAACCTTGGACGCGTGCGAGTATGGGGTGCCGCAGCAT
     L  G  Y  A  A  D  V  V  T  L  D  A  C  E  Y  G  V  P  Q  H
 481 CGTCGCCGTGTCTTCATCTTTCCTGCCGCAGACGGCCAGCGTATTGATCCTCCCCAACCG
     R  R  R  V  F  I  F  G  A  A  D  G  Q  R  I  D  P  P  Q  P
 541 TCTCACGTTAACGGTAAGCGTAGCGGTGTCGTGCTAAACGATCAGCCTTCGCTGTTCTTC
     S  H  V  N  G  K  R  S  G  V  V  L  N  D  Q  P  S  L  F  F
 601 GATGGTCCGTCGATCCAGCCAGCCTCTGACTGTTCGCGATGCTATTTCGGACCTAAGACC
     D  G  P  S  I  Q  P  A  L  T  V  R  D  A  I  S  D  L  P  D
 661 GAGGTGCTGGTGCCGCGTGACACTCAAAAACCGATGGAATATCCCGAGCCGCCTAAGACC
     E  V  L  V  P  R  D  T  Q  K  P  M  E  Y  P  E  P  P  K  T
 721 GAGTATCAGCGGTTGATGCGAGGTAATTCCACGGAGCTAACCCATCACTCGGCAAAAAGA
     E  Y  Q  R  L  M  R  G  N  S  T  E  L  T  H  H  S  A  K  R
 781 ATGTTAGGTATCCGCCGTTTACGGTTGGCGATGCTTCATCCTGGTGACTACGGGACCAAG
     M  L  G  I  R  R  L  R  L  A  M  L  H  P  G  D  Y  G  T  K
 841 ATCGAAGAACGGCTGGCTGACGGCGGCCTAAATGACGAGCTCATAGACTTGATGATGGGT
     I  E  E  R  L  A  D  G  G  L  N  D  E  L  I  D  L  M  M  G
 901 GGAGCTGGAATGCGCGATGCCGCAGAGTGCCGTACTCAGGACCGAGAAAAAGAGGCTGCC
     G  A  G  M  R  D  A  A  E  C  R  T  Q  D  R  E  K  E  A  A
 961 CTTCGGGAGGTGTTGAAGGGAGGCCATACCACACCTGCGAAGGTGATGGAATTCCTGGAT
     L  R  E  V  L  K  G  G  H  T  T  P  A  K  V  M  E  F  L  D
1021 AGTCAAGGGTTCGCAAACAAGTACCGTCGGTTACGCTGGGATGCACCATCGCACACGGTC
     S  Q  G  F  A  N  K  Y  R  R  L  R  W  D  A  P  S  H  T  V
1081 GTCGCGCACATGGCTCGGGATTGTTCAGACTTCGTGCACCCCGGCATTGATCGCTTCGTC
     V  A  H  M  A  R  D  C  S  D  F  V  H  P  G  I  D  R  F  V
1141 TCGGTGCGAGAGGCTGCAAGGTTCCAGTCTTTTCCTGACACCTATCGATTTCCAGGCTCG
     S  V  R  E  A  A  R  F  Q  S  F  P  D  T  Y  R  F  P  G  S
1201 CAGTTCCGCCAGTTCCGCCAAATTGGAAACGCAGTCCCACCGTTGCTAGGCAGGGCAATG
     Q  F  R  Q  F  R  Q  I  G  N  A  V  P  P  L  L  G  R  A  M
1261 GCTGAAACAATAAAGGTTGCGATCAGTTAG 1290
     A  E  T  I  K  V  A  I  S  *
```

FIG. 4

```
  1 ATGTGGTGTAATTATGAAGGCGGGGGATTTGACTTGAGATTGGACTTGGACTTCGGGCGT
    M  W  C  N  Y  E  G  G  G  F  D  L  R  L  D  L  D  F  G  R
 61 GGACTGGTCGCCCATGTGATGCTGGATAACGTAAGCGAGGAGCAGTACCAFCAAATCTCC
    G  L  V  A  H  V  M  L  D  N  V  S  E  E  Q  Y  Q  Q  I  S
121 GACTACTTCGTGCCGCTGGTCAACAAGCCGAAGCTTAAGAGCCGCGACGCTATCGGTCAG
    D  Y  F  V  P  L  V  N  K  P  L  K  S  R  D  A  I  G  Q
181 GCTTTCGTAATGGCGACGGAAGTCTGTCCGGACGCCAACCCCTCAGACCTCTGGCACCAC
    A  F  V  M  A  T  E  V  C  P  D  A  N  P  S  D  L  W  H  H
241 GTCTTGTACCGCATCTACATACGCGAGAAGATCGGAACCGACCCAAGCCAGAGCTGGGTT
    V  L  Y  R  I  Y  I  R  E  K  I  G  T  D  P  S  Q  S  W  V
301 CGCACGTCGGGCGAGGCCTTTGAGGTCGCGCTGGTCGAGCGTTATAATCCAGTGCTGGCC
    R  T  S  G  E  A  F  E  V  A  L  V  E  R  Y  N  P  V  L  A
361 CGACATGGGATCAGGTTGACCGCCTTATTCAAGGGGCAGAAGGGCCTTGCACTGACGCGT
    R  H  G  I  R  L  T  A  L  F  K  G  Q  K  G  L  A  L  T  R
421 ATGGGTGTGGCCGACCGCGTCGGCTCTCGCAAGGTTGACGTGATGATCGAGAAGCAGGGA
    M  G  V  A  D  R  V  G  S  R  K  V  D  V  M  I  E  K  Q  G
481 GGCGGACGCTCTCCGGACGCCGAGGGATTCGGCGTCGTGGGTGGCATCCACGCCAAGGTG
    G  G  R  S  P  D  A  E  G  F  G  V  V  G  G  I  H  A  K  V
541 AGCCTAGCCGAGAGGGTCTCGGACGACATACCCGCCAGCAGGATCATGATGGGCGAGGGT
    S  L  A  E  R  V  S  D  D  I  P  A  S  R  I  M  M  G  E  G
601 CTCCTCAGCGTGCTCTCCACCCTCGACGTCAAGTCGTTCCCTCCGCCCCACGGCGATTTG
    L  L  S  V  L  S  T  L  D  V  K  S  F  P  P  P  H  G  D  L
661 GTGAACCGAGGCGAGCTTGGCACGCCCGACCGGCCCTCGGACAAGAGGAATTACATTGAG
    V  N  R  G  E  L  G  T  P  D  R  P  S  D  K  R  N  Y  I  E
721 GGACACGGGGATTTCTCGGCCTGTTTCAGCTACAACCTGCGGACCCCGCCGTCCAACGCA
    G  H  G  D  F  S  A  C  F  S  Y  N  L  R  T  P  P  S  N  A
781 ACAACGCCCAGCGGACGCCACATATACGTGAGCGCTTCTCTGGTCAGGACGACGAGTTCA
    T  T  P  S  G  R  H  I  Y  V  S  A  S  L  V  R  T  T  S  S
841 CCGACTACTTAG 852
    P  T  T  *
```

5,885,818

METHOD FOR CLONING AND PRODUCING AGEI RESTRICTION ENDONUCLEASE IN E. COLI

BACKGROUND OF THE INVENTION

The present invention relates to recombinant DNA which encodes the AgeI restriction endonuclease as well as AgeI methyltransferase, and production of AgeI restriction endonuclease from *E. Coli* cells containing the recombinant DNA.

Type II restriction endonucleases are a class of enzymes that occur naturally in bacteria. When they are purified away from other bacterial proteins, restriction endonucleases can be used in the laboratory to cleave DNA molecules into small fragments for molecular cloning and gene characterization.

Restriction endonucleases act by recognizing and binding to particular sequences of nucleotides (the 'recognition sequence') along the DNA molecule. Once bound, they cleave the molecule within, to one side of, or to both sides of the recognition sequence. Different restriction endonucleases have affinity for different recognition sequences. Over two hundred and eleven restriction endonucleases with unique specificities have been identified among the many hundreds of bacterial species that have been examined to date (Roberts and Macelis, *Nucl. Acids Res.* 24:223–235, (1996)).

Restriction endonucleases typically are named according to the bacteria from which they are derived. Thus, the species *Deinococcus radiophilus* for example, produces three different restriction endonucleases, named DraI, DraII and DraIII. These enzymes recognize and cleave the sequences 5'TTTAAA3', 5'PuGGNCCPy3' and 5'CACNNNGTG3' respectively. *Escherichia coli* RY13, on the other hand, produces only one enzyme, EcoRI, which recognizes the sequence 5'GAATTC3'.

A second component of bacterial restriction-modification (R-M) systems are the methylases. These enzymes are complementary to restriction endonucleases and they provide the means by which bacteria are able to protect their own DNA and distinguish it from foreign, infecting DNA. Modification methylases recognize and bind to the same recognition sequence as the corresponding restriction endonuclease, but instead of cleaving the DNA, they chemically modify one particular nucleotide within the sequence by the addition of a methyl group ($C^5$ methyl cytosine, $N^4$ methyl cytosine, or $N^6$ methyl adenine). Following methylation, the recognition sequence is no longer cleaved by the cognate restriction endonuclease. The DNA of a bacterial cell is always fully modified by virtue of the activity of its modification methylase. It is therefore completely insensitive to the presence of the endogenous restriction endonuclease. It is only unmodified, and therefore identifiably foreign DNA, that is sensitive to restriction endonuclease recognition and cleavage.

With the advent of recombinant DNA technology, it is now possible to clone genes and overproduce the enzymes in large quantities. The key to isolating clones of restriction endonuclease genes is to develop a simple and reliable method to identify such clones within complex 'libraries', i.e. populations of clones derived by 'shotgun' procedures, when they occur at frequencies as low as $10^{-3}$ to $10^{-4}$. Preferably, the method should be selective, such that the unwanted majority of clones are destroyed while the desirable rare clones survive.

Type II restriction-modification systems are being cloned with increasing frequency. The first cloned systems used bacteriophage infection as a means of identifying or selecting restriction endonuclease clones (EcoRII: Kosykh et al., *Mol. Gen. Genet.* 178:717–719, (1980); HhaII: Mann et al., *Gene* 3:97–112, (1978); PstI: Walder et al., *Proc. Nat. Acad. Sci.* 78:1503–1507, (1981)). Since the presence of restriction-modification systems in bacteria enable them to resist infection by bacteriophages, cells that carry cloned restriction-modification genes can, in principle, be selectively isolated as survivors from libraries that have been exposed to phages. This method has been found, however, to have only limited value. Specifically, it has been found that cloned restriction-modification genes do not always manifest sufficient phage resistance to confer selective survival.

Another cloning approach involves transferring systems initially characterized as plasmid-borne into *E. coli* cloning plasmids (EcoRV: Bougueleret et al., *Nucl. Acids. Res.* 12:3659–3676, (1984); PaeR7: Gingeras and Brooks, *Proc. Natl. Acad. Sci. USA* 80:402–406, (1983); Theriault and Roy, *Gene* 19:355–359 (1982); PvuII: Blumenthal et al., *J. Bacteriol.* 164:501–509, (1985)).

A third approach, and one that is being used to clone a growing number of R-M systems are now being cloned by selection for an active methylase gene (U.S. Pat. No. 5,200,333, (1993) and BsuRI: Kiss et al., *Nucl. Acids. Res.* 13:6403–6421, (1985)). Since R-M genes are often closely linked, both genes can often be cloned simultaneously. This selection does not always yield a complete restriction system however, but instead yields only the methylase gene (BspRI: Szomolanyi et al., *Gene* 10:219–225, (1980); BcnI: Janulaitis et al., *Gene* 20:197–204 (1982); BsuRI: Kiss and Baldauf, *Gene* 21:111–119, (1983); and MspI: Walder et al., *J. Biol. Chem.* 258:1235–1241, (1983)).

A more recent method, the "endo-blue method", has been described for direct cloning of restriction endonuclease genes in *E. coli* based on the indicator strain of *E. coli* containing the dinD::lacZ fusion (Fomenkov et al., U.S. Pat. No. : 5,498,535, (1996); Fomenkov et al., *Nucl. Acids Res.* 22:2399–2403, (1994)). This method utilizes the *E. coli* SOS response following DNA damages caused by restriction endonucleases or non-specific nucleases. A number of thermostable nuclease genes (Tth111I, BsoBI, Tf nuclease) have been cloned by this method (U.S. Pat. No. : 5,498,535 (1996).

Because purified restriction endonucleases, and to a lesser extent, modification methylases, are useful tools for creating recombinant molecules in the laboratory, there is a commercial incentive to obtain bacterial strains through recombinant DNA techniques that produce these enzymes in large quantities. Such overexpression strains would also simplify the task of enzyme purification.

SUMMARY OF THE INVENTION

AgeI is a restriction endonuclease which recognizes the palindromic hexanucleotide sequence ACCGGT, cuts between the A and C, and forms a 5'-cohesive tetranucleotide extension (Yamada, et al.,*Agric. Biol. Chem.*, 53:1747–1749 (1989) and (Mizuno, et al., *Agric. Biol. Chem.*, 54:1797–1802 (1990)). Suzuki, et al., published the AgeI methylase gene sequence (*Biosci. Biotech. Biochem.*, 60:444–447 (1996)). They also published ~150 bp sequence downstream of ageIM gene, which is part of ageIR gene. In accordance with the present invention, we determined that their sequence contains a 13 bp deletion in the ageIR gene. This deletion would produce an inactive AgeI endonuclease if the deletion mutant had expressed in *E. coli*. Suzuki, et al., (supra) reported that cloning of 1 kb downstream sequence did not produce AgeI endonuclease activity. In fact, they analyzed the nucleotide sequence in both the upstream and downstream direction but did not find the open reading frame.

In accordance with the present invention, the methylase selection method was used to clone the AgeI methylase gene (ageIM) from *Agrobacterium gelatinovorum* (ATCC 25655). Two AgeI methylase plus (M⁺) clones were identified in a Sau3AI partial library. The entire insert (~5400 bp) from the AgeI M⁺ clones was completely sequenced. One open reading frame was identified that contains conserved $C^5$ cytosine methylase motifs and this gene was assigned ageIM gene. This clone however, did not produce AgeI restriction endonuclease. It was concluded that the AgeI endonuclease gene is probably truncated in the M⁺ clone due to the nature of Sau3AI partial digestion. Because methylase genes and restriction endonuclease genes are typically located in proximity to each other in a particular restriction-modification system, efforts were made to amplify and clone ageIM upstream and downstream DNA sequences by inverse PCR. After four rounds of inverse PCR reactions, one open reading frame (ORF1) was found upstream of the ageIM gene and another open reading frame (ORF2) was found downstream of the ageIM gene. Expression of ORF1 in a T7 expression vector did not yeld any AgeI restriction endonuclease activity. Expression of the second ORF (ORF2) in *E. coli* produced AgeI endonuclease activity. Thus, ORF2 was assigned as ageIR gene. The ageiR gene is 852 bp, encoding a protein with predicted molecular mass of 31,035 daltons.

BRIEF DESCRIPTION OF THE DRAWINGS

FIG. 1 shows the gene organization of AgeI restriction-modification system.

FIG. 2 is the ORF1 DNA sequence and its encoded amino acid sequence (SEQ ID NO:1).

FIG. 3 is the DNA sequence of ageIM gene and its encoded amino acid sequence (SEQ ID NO:2).

FIG. 4 is the DNA sequence of ageIR gene and its encoded amino acid sequence (SEQ ID NO:3).

DETAILED DESCRIPTION OF THE INVENTION

Figure 5:
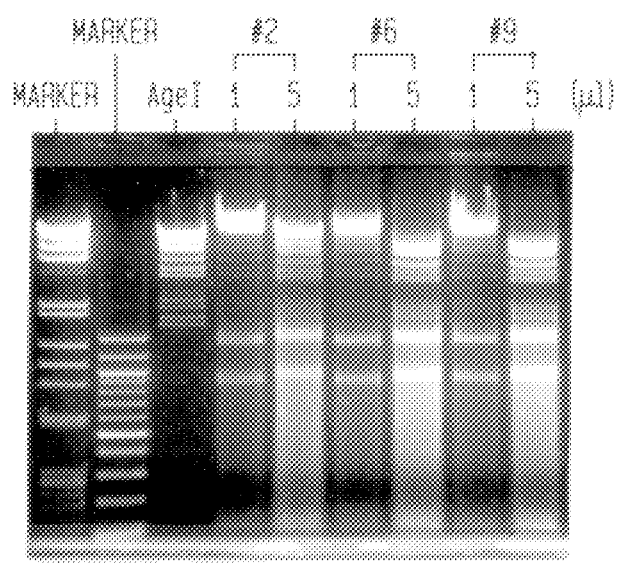
FIG. 5 is a photograph illustrating the restriction digestion using *E. coli* cell extract containing AgeI restriction endonuclease.

The method described herein by which the AgeI methylase gene and the AgeI restriction endonuclease genes are preferably cloned and expressed in *E. coli* utilizes the following steps:

1. Construction of a Sau3AI partial genomic DNA library.

*Agrobacterium gelatinovorum* (ATCC 25655) genomic DNA was digested with Sau3AI to achieve the desired partial digestion. The Sau3AI partially digested genomic DNA in the range of 0.5–20 kb was ligated into BamHI cut and CIP treated vector pAge-2; pUC19 derivative with two AgeI sites at 16° C. overnight. Transformation was carried out using RR1 competent cells and ligated DNA. The transformants were pooled and amplified. Plasmid DNA was prepared from the overnight cell cultures.

2. Challenge the Sau3AI partial library DNA with AgeI digestion and cloning of AgeI methylase gene (ageIM).

The Sau3AI partial library DNA was digested with AgeI at 37° C. overnight. The digested DNA was used to re-transform RR1 competent cells. Plasmid DNA was isolated from cell culture of all transformants. Individual plasmid DNA was digested with AgeI to detect any resistance to digestion. Two plasmids isolated, #1 and #26 displayed resistance to AgeI digestion. The degree of resistance to AgeI digestion was complete, suggesting that the clones contained the AgeI methylase gene and expressed in *E. coli*.

3. Sequencing of the insert carrying the AgeI methylase gene

Two M⁺ clones, #1 and #26 were subjected to DNA sequencing by primer walking. The entire insert of #26 was sequenced and found to overlap #1 completely. #26 insert has 5356 bp DNA with partial and complete open reading frames, however one large ORF was compared to the other genes in GenBank using blastx, and it shows homology to known $C^5$ cytosine methylases. This gene was assigned as ageiM gene. There are 3576 bp of DNA upstream of the ageIM gene and 491 bp of DNA downstream of the ageIM gene. Some of the sequences may be derived by random ligation of Sau3AI fragments during library construction. (In later experiments, it was found that the ageIR gene is located downstream of the ageIM gene, see FIG. 1).

4. Expression of AgeI methylase gene in *E. coli*

The entire AgeI methylase gene (1290 bp) was amplified from genomic DNA using Vent® DNA polymerase and two primers by PCR. The PCR product (ageIM gene) was digested with BamHI, gel-purified and cloned into pACYC184. Four plasmid isolates displayed full resistance to AgeI digestion, indicating modification of AgeI sites in vivo via the insertion and expression of the AgeI methylase gene.

5. Cloning and expression of AgeIM upstream sequence

There are 3576 bp of DNA upstream of the ageIM gene in the original M⁺ clone, but this clone does not produce AgeI endonuclease activity. It was reasoned that part of or all of the 3576 bp DNA were derived from random ligation. Inverse PCR was used to amplify and clone the continuous DNA upstream of ageIM gene. After two rounds of inverse PCR, one open reading frame (ORF1) of 681 bp was found (FIG. 2). ORF1 was amplified by PCR and cloned into a T7 expression vector pAII17 (pET11 derived) and transformed into AgeI methylase premodified host. *E. coli* cells were induced with IPTG and cell extract was assayed for AgeI activity. No AgeI activity was detected.

6. Cloning and expression of AgeI restriction endonuclease gene

Since restriction and modification genes are typically located in close proximity to each other, it was concluded that the ageIR gene is located downstream. Inverse PCR was used to amplify DNA downstream of ageIM gene. After two rounds of inverse PCR, one open reading frame (ORF2) of 852 bp was found. ORF2 is in opposite orientation as the ageIM gene (see FIG. 1 for the AgeI R-M gene organization). ORF2 was amplified by PCR and cloned into a T7 expression vector pAII17 and transformed into AgeI methylase premodified cells. *E. coli* cells were induced with IPTG for three hours and cell extracts were prepared and assayed for AgeI activity. Eight cell extracts were assayed and all of them displayed AgeI activity. Thus, ORF2 was assigned as ageIR gene (FIG. 4).

The present invention is further illustrated by the following Example. This Example is provided to aid in the understanding of the invention and is not construed as a limitation thereof.

The references cited above and below are incorporated herein by reference.

EXAMPLE 1

CLONING OF AGEI RESTRICTION-MODIFICATION SYSTEM IN E. COLI

Genomic DNA was prepared from *Agrobacterium gelatinovorum* (ATCC 25655) (this strain is in the New England Biolabs' collection, NEB #552, Beverly, Mass.); Yamada et al, *Agric. Biol. Chem.* 53:1747–1749 (1989).

1. Construction of a Sau3AI partial genomic DNA library

Four µg of Agrobacterium gelatinovorum genomic DNA was digested with 0.5, 0.25 and 0.125, 0.0625, 0.03, 0.015, 0.0078, 0.0039 units of Sau3AI at 37° C. for 15 min. All eight tubes of digestion were combined as partial digestion pool. The Sau3AI partially digested genomic DNA was in the range of 0.5–20 kb. The Sau3AI partially digested genomic DNA was ligated into BamHI cut and CIP treated vector pAge-2; pUC19 derivative with two AgeI sites (Skoglund et al, *Gene*, 88:1–5 (1990)) at 16° C. overnight.

pAge-2 contains an AgeI linker; (5'd(pGACCGGTC)3' 8 mer), at two different sites in pUC19 (Yanisch-Perron et al *Gene*, 33:103–119 (1985)); one at the SspI site and another at a DraI site between the β-lactamase gene and ori of pUC19. After the ligation reaction transformation was carried out by mixing RR1 (TonA⁻, DnaseI⁻) competent cells and the ligated DNA by the standard procedure. Transformants were plated on LB agar plus Amp (100 µg/ml). About 10,000 colonies were obtained in transformation. To increase the number of colonies, another 5× transformation was carried out using RR1 (TonA⁻, DnaseI⁻) cells and the ligated DNA. About 50,000 transformants were obtained. All the transformants were pooled and inoculated into 0.5 liter of LB broth plus Amp and incubated at 37° C. overnight. Plasmid DNA was prepared from the overnight cells by CsCl gradient.

2. Challenge the Sau3AI partial library DNA with AgeI digestion and cloning of AgeI methylase gene (ageIM)

Two µg of the Sau3AI partial library DNA was digested with 12 units of AgeI at 37° C. overnight. The digested DNA was used to re-transform RR1 (TonA⁻, DnaseI⁻) competent cells. Fourty-eight survivors were obtained. Mini-preparation of plasmid DNA was isolated from 10 ml cell culture of 28 transformants. Individual plasmid DNA was digested with AgeI to detect any resistance to digestion. Two plasmids isolated, #1 and #26 displayed resistance to AgeI digestion. The degree of resistance to AgeI digestion was complete, suggesting that the cloned AgeI methylase gene was complete and expressed in *E. coli* (sequencing the insert verified that the entire AgeI methylase gene was cloned).

Restriction digestion of #1 and #26 plasmid DNA with AatII, and Sau3AI indicated overlapping DNA. #1 contained a 1.8 kb partial Sau3AI fragment that was completely overlapped by #26 which contained a partial Sau3AI insert of approximately 5.4 kb of DNA.

3. Sequencing of the insert carrying the AgeI methylase gene

1 and #26 plasmid DNA were sequenced by primer walking using the dideoxy termination method using Ampli-Taq DNA polymerase dye deoxy terminator sequencing kit and ABI373A automated DNA sequencer. Primers were synthesized to sequence the non-overlapping region or to confirm the complementary strand of the known sequence. The entire insert of #26 was sequenced and found to contain 5356 bp of partial Sau3AI fragments that encode several partial and complete open reading frames. When the large ORF was compared to the known gene in GenBank using blastx, one of shows homology to known $C^5$ cytosine methylases. One orf upstream of ageIM gene shows weak homology to a known transposase; Tpase D78259. The downstream partial orf showed no homology to any gene in GenBank. The AgeI methylase gene nt 3577–4866 is encoded on 1290 bp of DNA and starts at the codon ATG (Met) and stops at TAG codon.

4. Expression of ageIM gene in *E. coli*

PCR was performed to amplify the ageIM gene. BamHI sites were engineered into the two primers 179-36 and 179-37 at the 5' ends. Ten PCR reactions were performed using 0.2 µg genomic DNA, 10 µl 10× Thermopol buffer, 0.27 mM concentration of dNTP, 79 µl H₂O, 0.12 µg primer 179-36, 0.12 µg primer 179-37, 2 units of Vent® DNA polymerase.

5' AACGGATCCGGAGGTTTAAAAATGAA-GACGATCGATCTATTTTGC 3'

(179-36) (SEQ ID NO:4)

5' CAAGGATCCTAACTGATCGCAACCTT-TATTGTTTCA 3' (179-37) (SEQ ID NO:5)

The resulting DNA was purified on low melting agarose gel and the DNA bands were cut out and extracted with equal amounts of phenol-CHCl₃ and CHCl₃ and precipitated with cold ethanol, dried and resuspended in 80 µl of TE buffer. The PCR DNA (approximately 4 µg) was then digested with 200 units of BamHI, 10 µl 10× BaHI buffer and incubated at 37° C. for 3 hours. The BamHI digested DNA was gel-purified and treated with β-agarase and extracted with equal amounts of phenol-CHCl₃ and CHCl₃ and precipitated with cold ethanol, dried and resuspended in 50 µl of TE buffer. The purified DNA was inserted into pACYC184. Fourteen mini-preparation of plasmid DNA was made and 11 of them contained the methylase gene insert. Digestion of six plasmids with AgeI indicated that four isolates (#1, #3, #4, #6) were resistant to AgeI digestion. #1 isolate was used to tranform the T7 expression host ER2566 to premodify chromosome DNA.

5. Cloning of DNA upstream of the ageIM gene

In 17 reactions 10 g genomic DNA was digested with AatII, ApoI, BanI, BsaHI, EaeI, Eco47III, HaeII, HincII, HpaI, MluI, MspI, NlaIII, PvuI, SacI, TaqI, Tsp509I, and XmnI. The resulting DNA was then extracted by equal volumes of phenol-CHCl₃ and CHCl₃, precipitated with cold ethanol, dried and resuspended in TE buffer. Two µg of the DNA was self-ligated with T4 DNA ligase then extracted with phenol-CHCl₃ and CHCl₃, precipitated with cold ethanol. A set of inverse PCR primers were synthesized:

5' AAGGGTGCTGAAGTACCCAAACGCCGG 3'

(178-44) (SEQ ID NO:6)

5' GCGGAGAACAGCCGCCACAGATGCGAC 3'

(178-45) (SEQ ID NO:7)

Inverse PCR was carried out using primers 178-44 and (178-45 and the above mentioned DNA template. Inverse PCR products were found in AatII, HincII, PvuI, TaqI, Tsp509I, and XmnI-digested and self-ligated DNA. Inverse PCR was repeated on these six reactions and the products were gel purified and sequenced directly using primers (178-44 and 178-45. The AatII fragment provided 449 bp of DNA sequence.

A second set of inverse PCR primers were synthesized:

5' TCGGGAAGCTGGGACCTTGCGAGC 3'

(178-122) (SEQ ID NO:8)

5' ACCACCTATATCGCCACCGCACCT 3'

(178-123) (SEQ ID NO:9)

Ten µg genomic DNA was digested with AatII, ApoI, AvaI, ApaLI, BsaHI, BstUI, HaeII, PvuI, Sau3AI, StyI, and TaqI. The resulting DNA was then extracted by equal volumes of phenol-CHCl$_3$ and CHCl$_3$, precipitated with cold ethanol, dried and resuspended in TE buffer. Two μg of the DNA was self-ligated with T4 DNA ligase then extracted with phenol-CHCl$_3$ and CHCl$_3$, precipitated with cold ethanol. Inverse PCR was carried out using primers 178-122 and 178-123 and the above mentioned template DNA. PCR products were found in BsaHI and TaqI template. The inverse PCR DNA was repeated with three tubes each and the products were gel purified in low melting agarose gel. The DNA was sequenced directly using primers 178-122 and 178-123. One open reading frame of 681 bp was found. This ORF was named ORF1.

6. Expression of ORF1 in T7 expression vector A set of PCR primers were synthesized:

5' CTTCCCGACCATATGGGGCCAT-CAACGCTGAAAAGGAGA 3'
(181-184) (SEQ ID NO:10)
5' GCTGGATCCTCAGCGAGGATATTTGCA-GACACCATA 3'
(179-100) (SEQ ID NO:11)

ORFI was amplified by PCR using primers 181–184 and 179-100 from AgeI genomic DNA under PCR conditions of 95° C. 30 seconds, 55° C. 1 minute and 72° C. 1 minute, and 2 units Vent® DNA polymerase for 20 cycles. The PCR product was digested with NdeI and BamHI and cloned into T7 expression vector pAII17. The ligated DNA was transformed into T7 expression host ER2566 [pACYC-AgeIM$^+$]. Plasmid DNA was isolated from 20 transformants and digested with NdeI and BamHI to screen for insert. Ten out of 20 contained the insert. Seven clones with insert were induced with IPTG for 2 hours. Cell extacts were prepared and assayed for AgeI restriction endonuclease activity. No activity was detected in all 7 extracts. It was concluded that ORF1 is not the AgeI endonuclease gene. The AgeI endonuclease gene must be located downstream of the methylase gene.

7. Amplification of downstream DNA by inverse PCR

One set of PCR primers based on the sequence immediately downstream of the AgeI methylase gene were synthesized:

5' AACTCGTCGTCCTGACCAGAGAAG 3'
(182-159) (SEQ ID NO:12)
5' CGACTACTTAGTCGCCCAACTGGC 3'
(182-160) (SEQ ID NO:13)

A second set of PCR primers 165 bp downstream of AgeI methylase gene were synthesized:

5' TAATTCCTCTTGTCCGAGGGCCGG 3'
(182-161) (SEQ ID NO:14)
5' ATTGAGGGACACGGGGATTTCTCG 3'
(182-162) (SEQ ID NO:15)

Ten μg genomic DNA was digested with AvaII, BsrBI, ClaI, DdeI, EcoRI, HhaI, NciI, TseI and NruI. The resulting DNA was then extracted by equal volumes of phenol-CHCl$_3$ and CHCl$_3$, precipitated with cold ethanol, dried and resuspended in TE buffer. Two μg of the DNA was self-ligated with T4 DNA ligase then extracted with phenol-CHCl$_3$ and CHCl$_3$, precipitated with cold ethanol. Inverse PCR was carried out using primers 182-161 and 182-162. Inverse PCR products were found in HhaI and TseI DNA. These two PCR reactions were repeated with four tubes each. The PCR DNA was gel purified from low melting agarose gel and sequenced directly using primers 182-161 and 182-162. The HhaI fragment provided 341 bp of new sequence. A set of inverse PCR primers were synthesized:

5' CCCATGTCGGGCCAGCACTGGATT 3'
(183-88) (SEQ ID NO:16)
5' ACTAGGTTGACCGCCTTATTCAAG 3'
(183-89) (SEQ ID NO:17)

Ten μg genomic DNA was digested with AatII, AflIII, AluI, ApaLI, AvaI, BarBI, BfaI, BsaAI, BsaWI, BsiEI, BspEI, BspHI, BstUI, DdeI, HinfI, HpaII, MluI, MspI, StyI, TaiI, TfiI, and Tsp509I. The resulting DNA was then extracted by equal volumes of phenol-CHCl$_3$ and CHCl$_3$, precipitated with cold ethanol, dried and resuspended in TE buffer. Two μg of the DNA was self-ligated with T4 DNA ligase then extracted with phenol-CHCl$_3$ and CHCl$_3$, precipitated with cold ethanol. PCR products were found in BsaWI and TaiI digested and self ligated DNA. The above PCR reaction was repeated with BsaWI and TaiI. Approximately 50 ng of template DNA was combined with 68 μl of H$_2$O, 10 μl 10× Taq polymerase buffer, 5.4 μl of 5 mm dNTP (final concentration 0.27 mM), 0.12 μg primer 183-88, 0.12 μg primer 183-89, 2.5 units Taq DNA polymerase.

5' CCCATGTCGGGCCAGCACTGGATT 3'
(183-88) (SEQ ID NO:18)
5' ATCAGGTTGACCGCCTTATTCAAG 3'
(183-89) (SEQ ID NO:19)

The PCR reactions were carried out for thirty cycles of 95° C. for 30 seconds, 60° C. for 30 seconds and 72° C. for 1 minute with a 5 minutes hold after completion of the cycles then sequenced. The BsaWI IPCR product was approximately 300 bp and the TaiI product 170 bp and the two products were purified on low melting agarose gel. IPCR was also repeated on AflIII, AluI, BfaI, BsaAI, BsiEI, BspEI, BspHI, BsrBI, BstUI, DdeI, HinfI, HpaII, StyI, TfiI and Tsp509I digested and self-ligated DNA templates. Approximately 50 ng of template DNA was combined with 68 μl H$_2$), 10 μl 10× Taq polymerase buffer, 0.27 mM concentration dNTP, 0.12 μg primer 183-88, 0.12 μg primer 183-89, 2.5 units of Taq DNA polymerase. The reactions underwent a 95° C. preheat, then thirty cycles of 95° C. for 30 seconds, 60° C. for 30 seconds and 72° C. for 1 minute with a 5 minute 72° C. hold after the completion of the cycles. The AflIII, AluI, BspEI, HpaII and Tsp509I templates generated approximately 300–600 bp of PCR products. The experiment was repeated with three tubes each for these five templates and was then gel purified and sequenced. The AflIII product was the longest with 578 bp and contained a TGA stop codon on the complementary strand 371 bp downstream.

PCR and DNA sequencing were performed to clear up ambiguous sequence, using primer 182-159 with 183-89 and primer 182-161 with 183-89 and two different concentrations of MgCl$_2$ (1.5 and 3.0 mM), 1 μg genomic DNA, 70 μl H$_2$O, 10 μl 10× Assay buffer A, 5.4 mM conc. dNTP, 0.12 μg of each primer, and 2.5 units Taq DNA polymerase.

5' AACTCGTCGTCCTGACCAGAGAAG 3'
(182-159) (SEQ ID NO:20)
5' TAATTCCTCTTGTCCGAGGGCCGG 3'
(182-161) (SEQ ID NO:21)

The PCR reactions were carried out for 30 cycles of 94° C. for 30 seconds, 55° C. for 30 seconds, 72° C. for 30 seconds, and a final 2 minutes 72° C. hold. Resulting DNA was subjected to electrophoresis on low melting agarose gel, the DNA bands were cut out and digested with β-agarase and precipitated with equal volumes of isopropanol, dried and resuspended in TE. The PCR DNA was sequenced directly using primers 182-159, 182-161 and 183-89. The ageIR gene is 852 bp, running in the opposite direction to the ageIM gene.

8. Expression of ageIR gene in *E. coli*

Two primers were constructed which engineered a BamHI and NdeI site into the 5' ends of the primers. PCR was completed in five reactions using 1 μg genomic DNA, 0.12 μg primer 184-53 (containing the NdeI site), 0.12 μg primer 184-54 (containing the BamHI site), 70 μl H$_2$O, 10 μl 10× Thermopol buffer, 0.27 mM conc. dNTP, 2 units Vent® DNA polymerase, and 0, 2, 4, 6, and 8 μl of 100 mM MgSO$_4$ for a 2, 4, 6, 8, and 10 mM final concentration of MgSO$_4$.

5' ATTTGCCCCATATGTGGTGTAATTAT- GAAGGCGGGGGA 3'

(184-53) (SEQ ID NO:22)

5' CGCGGATCCGAAACGCAGTCCCACCGTTGCTAG 3'

(184-54) (SEQ ID NO:23)

Twenty cycles at 94° C. for 30 seconds, 60° C. for 30 seconds, 72° C. for 1 minute, with a final hold of 72° C. for 2 minutes were completed. The 2 mM concentration of MgSO$_4$ gave the best results and the reaction was repeated with ten tubes. The resulting DNA was purified from a low melting gel and digested with β-agarase. The DNA was then precipitated with equal volumes of isopropanol, dried and resuspended in TE. Approximately 4 μg of the precipitated DNA was then digested with 200 units of NdeI, 100 units of BamHI in 22 μl 10× NEB buffer 3. The DNA was extracted with equal volume of phenol-CHCl$_3$ and CHCl$_3$ and precipitated with cold ethanol, dried and resuspended in 50 μl of TE buffer. The resulting DNA was then ligated in two reactions into 100 ng of vector pAII17, using 0.1 μg and 0.2 μg of PCR DNA (ageIR gene) respectively, 2 μl 10× T4 ligation buffer, 800 units T4 DNA ligase and incubated at 16° C. overnight. All of the recombinant DNA from the ligation was then transformed into 150 μl competent ER2566 cells by 30 minutes at 4° C., 3 minutes at 37° C. and 5 minutes at 25° C. After addition of 170 gl of SOB broth and incubation at 37° C. for 1 hour, the cell/DNA mixture was plated on LB agar plate plus 100 μg/ml Ampicillin (Ap) and 33 μg/ml Chloramphenacol (Cm) and incubated at 37° C. overnight. The 12 individual Ap and Cm resistant transformants that grew were picked and inoculated into 2 ml of LB+Ap+Cm and shaken at 37° C. overnight. 1.5 ml of cells were centrifuged to make plasmid DNA by Qiagen mini-preparation purification. 25 μl (~200 ng) of the resulting purified plasmid DNA was digested with 20 units BamHI, 20 units NdeI, in 3 μl 10× NEB buffer 3 and incubated at 37° C. for 1 hour. Eight of twelve showed AgeIR gene insert. Eight clones with insert were cultured in 10 ml LB+Ap+Cm to late log phase, 50 μl 100 mM IPTG was added and incubated at 37° C. overnight. IPTG induced cells were harvested and resuspended in 1 ml sonification buffer and sonificated 3× 20 seconds each, then centrifuged 15 minutes at 4° C. The cell extract was assayed for restriction endonuclease activity by digesting 1 μg λDNA with 1 μl and 5 μl respectively of cell extract in 3 μl 10× NEB buffer 1 and incubated at 25° C. for 1 hour. All eight samples showed AgeI activity. ER2566 [pACYC-AgeIM$^+$, pAII17-AgeIR$^+$] strain has been deposited with the American Type Culture Collection on Apr. 1, 1998 and received Accession No. 209730

9. Purification of AgeI restriction endonuclease.

Two protocols can be used to purify AgeI.

Protocol 1: heparin Sepharose® column, hydroxylapatite column, Mono S column, tsk heparin column.

Protocol 2: heparin Sepharose® column, DEAE Sepharose® column, hydroxylapatite column, phenyl Sepharose® column.

---

What is claimed is:

1. Isolated DNA coding for the AgeI restriction endonuclease, wherein the isolated DNA is obtainable from *Agrobacterium gelatinovorum*.

2. A recombinant DNA vector comprising a vector into which a DNA segment encoding the AgeI restriction endonuclease has been inserted.

3. Isolated DNA encoding the AgeI restriction endonuclease and methylase, wherein the isolated DNA is obtainable from ATCC No. 209730.

4. A cloning vector which comprises the isolated DNA of claim 3.

5. A host cell transformed by the cloning vector of claims 2 or 4.

6. A method of producing AgeI restriction endonuclease comprising culturing a host cell transformed with the vector of claims 2 or 4 under conditions suitable for expression of said endonuclease.

* * * * *

UNITED STATES PATENT AND TRADEMARK OFFICE
CERTIFICATE OF CORRECTION

PATENT NO. : 5,885,818

DATED : March 23, 1999

INVENTOR(S) : Shuang-yong Xu, Robert E. Maunus, Keith D. Lunnen and Rachel Allen It is certified that error appears in the above-identified patent and that said Letters Patent is hereby corrected as shown below:

```
Column 7, line 42    replace "were" with --was--
Column 8, line 2     replace "were" with --was--
```

Signed and Sealed this

Twenty-eighth Day of March, 2000

Attest:

Q. TODD DICKINSON

Attesting Officer

Commissioner of Patents and Trademarks

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 681 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: Coding Sequence
        ( B ) LOCATION: 1...678
        ( D ) OTHER INFORMATION:

( x i ) SEQUENCE DESCRIPTION: SEQ ID NO:1:

```
ATG  GGG  CCA  TCA  ACG  CTG  AAA  AGG  AGA  AAA  CCA  ATG  ACC  AAA  ACC  ACC        48
Met  Gly  Pro  Ser  Thr  Leu  Lys  Arg  Arg  Lys  Pro  Met  Thr  Lys  Thr  Thr
 1              5                        10                       15

TAT  ATC  GCC  ACC  GCA  CCT  GAT  GGA  TCG  GAA  CTC  ACT  CGC  AAG  ACC  GAC        96
Tyr  Ile  Ala  Thr  Ala  Pro  Asp  Gly  Ser  Glu  Leu  Thr  Arg  Lys  Thr  Asp
                 20                       25                      30

CGA  ACC  TAC  ACC  CAC  GCG  GTC  TTG  TTA  GAG  GGC  AAG  GAG  GGC  TGG  AAA       144
```

| | | | | | | | | | | | | | | | |
|---|---|---|---|---|---|---|---|---|---|---|---|---|---|---|---|
| Arg | Thr | Tyr | Thr | His | Ala | Val | Leu | Leu | Glu | Gly | Lys | Glu | Gly | Trp | Lys |
| | | 35 | | | | | 40 | | | | 45 | | | | |

```
GCT  GAG  GGG  TTC  TGC  GGA  CGT  CTC  GAC  CTG  GCC  CAC  AAG  AAG  CAA  CTT        192
Ala  Glu  Gly  Phe  Cys  Gly  Arg  Leu  Asp  Leu  Ala  His  Lys  Lys  Gln  Leu
     50                  55                       60

GAG  CAT  CCT  GGC  AGT  ATC  GTC  GTG  GAA  GTC  AAA  GCG  CTC  GGT  GAC  GCA        240
Glu  His  Pro  Gly  Ser  Ile  Val  Val  Glu  Val  Lys  Ala  Leu  Gly  Asp  Ala
65                       70                  75                            80

CAG  ACC  GAC  AAG  CCT  AAG  GCC  GAA  GCT  ACC  GAA  GAC  GCT  GAA  CCG  ACC        288
Gln  Thr  Asp  Lys  Pro  Lys  Ala  Glu  Ala  Thr  Glu  Asp  Ala  Glu  Pro  Thr
               85                       90                       95

AAA  GAT  GAG  ACG  GTT  GGA  CGC  CCC  GAA  GAA  GAG  CCG  AGC  GTC  GAT  GAG        336
Lys  Asp  Glu  Thr  Val  Gly  Arg  Pro  Glu  Glu  Glu  Pro  Ser  Val  Asp  Glu
               100                      105                     110

AAA  ATC  AGG  AAC  GCA  AAG  GTT  ACA  GGT  CCC  GAG  CGC  AAG  GGC  AAA  ATC        384
Lys  Ile  Arg  Asn  Ala  Lys  Val  Thr  Gly  Pro  Glu  Arg  Lys  Gly  Lys  Ile
               115                      120                     125

GGA  GAC  CTT  GTG  CAC  GAG  TTG  TTG  ATG  GAC  GAG  ACG  TTG  GAT  TAT  GTG        432
Gly  Asp  Leu  Val  His  Glu  Leu  Leu  Met  Asp  Glu  Thr  Leu  Asp  Tyr  Val
     130                      135                      140

ACG  ATC  GTG  GAT  CGG  GTC  ATG  GCA  AAT  TTC  CTG  ATG  CCA  AAA  CCA  CGG        480
Thr  Ile  Val  Asp  Arg  Val  Met  Ala  Asn  Phe  Leu  Met  Pro  Lys  Pro  Arg
145                      150                      155                      160

CAC  GTT  CAG  TCG  CAT  CTG  TGG  CGG  CTG  TTC  TCC  GCA  AGA  AGG  GTG  CTG        528
His  Val  Gln  Ser  His  Leu  Trp  Arg  Leu  Phe  Ser  Ala  Arg  Arg  Val  Leu
                    165                      170                      175

AAG  TAC  CCA  AAC  GCC  GGA  AAT  CCA  AGG  TAT  GAC  CTC  ATG  CGG  GCA  ACT        576
Lys  Tyr  Pro  Asn  Ala  Gly  Asn  Pro  Arg  Tyr  Asp  Leu  Met  Arg  Ala  Thr
               180                      185                      190

TGC  CGA  AAG  GGG  CGT  TGT  CAC  TGG  TCT  AGT  GGC  GAC  GTC  CTC  AAT  ATA        624
Cys  Arg  Lys  Gly  Arg  Cys  His  Trp  Ser  Ser  Gly  Asp  Val  Leu  Asn  Ile
          195                      200                      205

TTT  GGC  GTT  CCG  TTG  GTC  ATT  CAT  ACC  CGA  TAT  GGT  GTC  TGC  AAA  TAT        672
Phe  Gly  Val  Pro  Leu  Val  Ile  His  Thr  Arg  Tyr  Gly  Val  Cys  Lys  Tyr
210                      215                      220

CCT  CGC  TGA                                                                         681
Pro  Arg
225
```

(2) INFORMATION FOR SEQ ID NO:2:

(i) SEQUENCE CHARACTERISTICS:
        (A) LENGTH: 1290 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...1287
        (D) OTHER INFORMATION:

(xi) SEQUENCE DESCRIPTION: SEQ ID NO:2:

```
ATG  AAG  ACG  ATC  GAT  CTA  TTT  TGC  GGG  GCT  GGA  GGA  TTA  GGA  GAA  GGC         48
Met  Lys  Thr  Ile  Asp  Leu  Phe  Cys  Gly  Ala  Gly  Gly  Leu  Gly  Glu  Gly
1                   5                        10                           15

TTT  AGA  CAG  GCA  GGA  TTT  TCA  GCG  CTG  TAC  GCC  AAT  GAC  CAT  GAG  ACC         96
Phe  Arg  Gln  Ala  Gly  Phe  Ser  Ala  Leu  Tyr  Ala  Asn  Asp  His  Glu  Thr
               20                       25                      30

CCT  GCG  CTT  GCA  ACA  TAC  AAG  GAA  AAC  CAT  CCA  GAC  GCA  GTA  TGC  TCG        144
Pro  Ala  Leu  Ala  Thr  Tyr  Lys  Glu  Asn  His  Pro  Asp  Ala  Val  Cys  Ser
          35                       40                      45
```

```
ACT  GAT  TCC  ATC  GAG  ACT  GTA  GAC  CCC  AAG  AAA  ATT  CGC  GAA  GAC  CTT       192
Thr  Asp  Ser  Ile  Glu  Thr  Val  Asp  Pro  Lys  Lys  Ile  Arg  Glu  Asp  Leu
 50             55                            60

GGC  GTC  GCG  CCT  GGA  CAG  GTT  GAC  GTG  GTT  ATG  GGG  GGG  CCT  CCC  TGT       240
Gly  Val  Ala  Pro  Gly  Gln  Val  Asp  Val  Val  Met  Gly  Gly  Pro  Pro  Cys
 65                    70                       75                             80

CAA  GGC  TTC  TCA  ACC  TAC  GGG  CAG  CGA  CGC  GAC  GAC  GAT  GCG  AGG  AAC       288
Gln  Gly  Phe  Ser  Thr  Tyr  Gly  Gln  Arg  Arg  Asp  Asp  Asp  Ala  Arg  Asn
                     85                       90                          95

CAA  CTG  TAC  GTC  CCG  TAT  TTC  GGT  TTC  GTT  GAA  GAG  TTC  CGA  CCT  AAG       336
Gln  Leu  Tyr  Val  Pro  Tyr  Phe  Gly  Phe  Val  Glu  Glu  Phe  Arg  Pro  Lys
               100                      105                           110

GCA  TTT  CTG  ATC  GAG  AAC  GTG  GTC  GGG  TTG  CTC  TCA  ATG  TCT  GGA  GGC       384
Ala  Phe  Leu  Ile  Glu  Asn  Val  Val  Gly  Leu  Leu  Ser  Met  Ser  Gly  Gly
          115                      120                      125

GCG  GTA  CTT  GCA  GAC  ATG  GTC  GCC  CGC  GCA  GAG  GCA  CTC  GGT  TAT  GCT       432
Ala  Val  Leu  Ala  Asp  Met  Val  Ala  Arg  Ala  Glu  Ala  Leu  Gly  Tyr  Ala
     130                      135                      140

GCT  GAC  GTG  GTA  ACC  TTG  GAC  GCG  TGC  GAG  TAT  GGG  GTG  CCG  CAG  CAT       480
Ala  Asp  Val  Val  Thr  Leu  Asp  Ala  Cys  Glu  Tyr  Gly  Val  Pro  Gln  His
145                      150                      155                            160

CGT  CGC  CGT  GTC  TTC  ATC  TTT  GGT  GCC  GCA  GAC  GGC  CAG  CGT  ATT  GAT       528
Arg  Arg  Arg  Val  Phe  Ile  Phe  Gly  Ala  Ala  Asp  Gly  Gln  Arg  Ile  Asp
                    165                      170                           175

CCT  CCC  CAA  CCG  TCT  CAC  GTT  AAC  GGT  AAG  CGT  AGC  GGT  GTC  GTG  CTA       576
Pro  Pro  Gln  Pro  Ser  His  Val  Asn  Gly  Lys  Arg  Ser  Gly  Val  Val  Leu
               180                      185                      190

AAC  GAT  CAG  CCT  TCG  CTG  TTC  TTC  GAT  GGT  CCG  TCG  ATC  CAG  CCA  GCT       624
Asn  Asp  Gln  Pro  Ser  Leu  Phe  Phe  Asp  Gly  Pro  Ser  Ile  Gln  Pro  Ala
               195                      200                      205

CTG  ACT  GTT  CGC  GAT  GCT  ATT  TCG  GAC  CTG  CCT  GAT  GAG  GTG  CTG  GTG       672
Leu  Thr  Val  Arg  Asp  Ala  Ile  Ser  Asp  Leu  Pro  Asp  Glu  Val  Leu  Val
     210                      215                      220

CCG  CGT  GAC  ACT  CAA  AAA  CCG  ATG  GAA  TAT  CCC  GAG  CCG  CCT  AAG  ACC       720
Pro  Arg  Asp  Thr  Gln  Lys  Pro  Met  Glu  Tyr  Pro  Glu  Pro  Pro  Lys  Thr
225                      230                      235                            240

GAG  TAT  CAG  CGG  TTG  ATG  CGA  GGT  AAT  TCC  ACG  GAG  CTA  ACC  CAT  CAC       768
Glu  Tyr  Gln  Arg  Leu  Met  Arg  Gly  Asn  Ser  Thr  Glu  Leu  Thr  His  His
                    245                      250                           255

TCG  GCA  AAA  AGA  ATG  TTA  GGT  ATC  CGC  CGT  TTA  CGG  TTG  GCG  ATG  CTT       816
Ser  Ala  Lys  Arg  Met  Leu  Gly  Ile  Arg  Arg  Leu  Arg  Leu  Ala  Met  Leu
               260                      265                      270

CAT  CCT  GGT  GAC  TAC  GGG  ACC  AAG  ATC  GAA  GAA  CGG  CTG  GCT  GAC  GGC       864
His  Pro  Gly  Asp  Tyr  Gly  Thr  Lys  Ile  Glu  Glu  Arg  Leu  Ala  Asp  Gly
          275                      280                      285

GGC  CTA  AAT  GAC  GAG  CTC  ATA  GAC  TTG  ATG  ATG  GGT  GGA  GCT  GGA  ATG       912
Gly  Leu  Asn  Asp  Glu  Leu  Ile  Asp  Leu  Met  Met  Gly  Gly  Ala  Gly  Met
     290                      295                      300

CGC  GAT  GCC  GCA  GAG  TGC  CGT  ACT  CAG  GAC  CGA  GAA  AAA  GAG  GCT  GCC       960
Arg  Asp  Ala  Ala  Glu  Cys  Arg  Thr  Gln  Asp  Arg  Glu  Lys  Glu  Ala  Ala
305                      310                      315                            320

CTT  CGG  GAG  GTG  TTG  AAG  GGA  GGC  CAT  ACC  ACA  CCT  GCG  AAG  GTG  ATG      1008
Leu  Arg  Glu  Val  Leu  Lys  Gly  Gly  His  Thr  Thr  Pro  Ala  Lys  Val  Met
                    325                      330                           335

GAA  TTC  CTG  GAT  AGT  CAA  GGG  TTC  GCA  AAC  AAG  TAC  CGT  CGG  TTA  CGC      1056
Glu  Phe  Leu  Asp  Ser  Gln  Gly  Phe  Ala  Asn  Lys  Tyr  Arg  Arg  Leu  Arg
               340                      345                      350

TGG  GAT  GCA  CCA  TCG  CAC  ACG  GTC  GTC  GCG  CAC  ATG  GCT  CGG  GAT  TGT      1104
Trp  Asp  Ala  Pro  Ser  His  Thr  Val  Val  Ala  His  Met  Ala  Arg  Asp  Cys
          355                      360                      365
```

| | | | | | | | | | | | | | | | | |
|---|---|---|---|---|---|---|---|---|---|---|---|---|---|---|---|---|
|TCA|GAC|TTC|GTG|CAC|CCC|GGC|ATT|GAT|CGC|TTC|GTC|TCG|GTG|CGA|GAG|1152|
|Ser|Asp|Phe|Val|His|Pro|Gly|Ile|Asp|Arg|Phe|Val|Ser|Val|Arg|Glu| |
| |370| | | |375| | | |380| | | | | | | |

|GCT|GCA|AGG|TTC|CAG|TCT|TTT|CCT|GAC|ACC|TAT|CGA|TTT|CCA|GGC|TCG|1200|
|---|---|---|---|---|---|---|---|---|---|---|---|---|---|---|---|---|
|Ala|Ala|Arg|Phe|Gln|Ser|Phe|Pro|Asp|Thr|Tyr|Arg|Phe|Pro|Gly|Ser| |
|385| | | | |390| | | | |395| | | | |400| |

|CAG|TTC|CGC|CAG|TTC|CGC|CAA|ATT|GGA|AAC|GCA|GTC|CCA|CCG|TTG|CTA|1248|
|---|---|---|---|---|---|---|---|---|---|---|---|---|---|---|---|---|
|Gln|Phe|Arg|Gln|Phe|Arg|Gln|Ile|Gly|Asn|Ala|Val|Pro|Pro|Leu|Leu| |
| | | | | |405| | | | |410| | | | |415| |

|GGC|AGG|GCA|ATG|GCT|GAA|ACA|ATA|AAG|GTT|GCG|ATC|AGT|TAG| | |1290|
|---|---|---|---|---|---|---|---|---|---|---|---|---|---|---|---|---|
|Gly|Arg|Ala|Met|Ala|Glu|Thr|Ile|Lys|Val|Ala|Ile|Ser| | | | |
| | | |420| | | | |425| | | | | | | | |

( 2 ) INFORMATION FOR SEQ ID NO:3:

( i ) SEQUENCE CHARACTERISTICS:
        ( A ) LENGTH: 852 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: Coding Sequence
        ( B ) LOCATION: 1...849
        ( D ) OTHER INFORMATION:

( x i ) SEQUENCE DESCRIPTION: SEQ ID NO:3:

|ATG|TGG|TGT|AAT|TAT|GAA|GGC|GGG|GGA|TTT|GAC|TTG|AGA|TTG|GAC|TTG|48|
|---|---|---|---|---|---|---|---|---|---|---|---|---|---|---|---|---|
|Met|Trp|Cys|Asn|Tyr|Glu|Gly|Gly|Gly|Phe|Asp|Leu|Arg|Leu|Asp|Leu| |
|1| | | |5| | | | |10| | | | |15| | |

|GAC|TTC|GGG|CGT|GGA|CTG|GTC|GCC|CAT|GTG|ATG|CTG|GAT|AAC|GTA|AGC|96|
|---|---|---|---|---|---|---|---|---|---|---|---|---|---|---|---|---|
|Asp|Phe|Gly|Arg|Gly|Leu|Val|Ala|His|Val|Met|Leu|Asp|Asn|Val|Ser| |
| | | |20| | | | |25| | | | |30| | | |

|GAG|GAG|CAG|TAC|CAG|CAA|ATC|TCC|GAC|TAC|TTC|GTG|CCG|CTG|GTG|AAC|144|
|---|---|---|---|---|---|---|---|---|---|---|---|---|---|---|---|---|
|Glu|Glu|Gln|Tyr|Gln|Gln|Ile|Ser|Asp|Tyr|Phe|Val|Pro|Leu|Val|Asn| |
| | | |35| | | | |40| | | | |45| | | |

|AAG|CCG|AAG|CTT|AAG|AGC|CGC|GAC|GCT|ATC|GGT|CAG|GCT|TTC|GTA|ATG|192|
|---|---|---|---|---|---|---|---|---|---|---|---|---|---|---|---|---|
|Lys|Pro|Lys|Leu|Lys|Ser|Arg|Asp|Ala|Ile|Gly|Gln|Ala|Phe|Val|Met| |
| |50| | | | |55| | | | |60| | | | | |

|GCG|ACG|GAA|GTC|TGT|CCG|GAC|GCC|AAC|CCC|TCA|GAC|CTC|TGG|CAC|CAC|240|
|---|---|---|---|---|---|---|---|---|---|---|---|---|---|---|---|---|
|Ala|Thr|Glu|Val|Cys|Pro|Asp|Ala|Asn|Pro|Ser|Asp|Leu|Trp|His|His| |
|65| | | | |70| | | | |75| | | | |80| |

|GTC|TTG|TAC|CGC|ATC|TAC|ATA|CGC|GAG|AAG|ATC|GGA|ACC|GAC|CCA|AGC|288|
|---|---|---|---|---|---|---|---|---|---|---|---|---|---|---|---|---|
|Val|Leu|Tyr|Arg|Ile|Tyr|Ile|Arg|Glu|Lys|Ile|Gly|Thr|Asp|Pro|Ser| |
| | | | |85| | | | |90| | | | |95| | |

|CAG|AGC|TGG|GTT|CGC|ACG|TCG|GGC|GAG|GCC|TTT|GAG|GTC|GCG|CTG|GTC|336|
|---|---|---|---|---|---|---|---|---|---|---|---|---|---|---|---|---|
|Gln|Ser|Trp|Val|Arg|Thr|Ser|Gly|Glu|Ala|Phe|Glu|Val|Ala|Leu|Val| |
| | | |100| | | | |105| | | | |110| | | |

|GAG|CGT|TAT|AAT|CCA|GTG|CTG|GCC|CGA|CAT|GGG|ATC|AGG|TTG|ACC|GCC|384|
|---|---|---|---|---|---|---|---|---|---|---|---|---|---|---|---|---|
|Glu|Arg|Tyr|Asn|Pro|Val|Leu|Ala|Arg|His|Gly|Ile|Arg|Leu|Thr|Ala| |
| | | |115| | | | |120| | | | |125| | | |

|TTA|TTC|AAG|GGG|CAG|AAG|GGC|CTT|GCA|CTG|ACG|CGT|ATG|GGT|GTG|GCC|432|
|---|---|---|---|---|---|---|---|---|---|---|---|---|---|---|---|---|
|Leu|Phe|Lys|Gly|Gln|Lys|Gly|Leu|Ala|Leu|Thr|Arg|Met|Gly|Val|Ala| |
| |130| | | | |135| | | | |140| | | | | |

|GAC|CGC|GTC|GGC|TCT|CGC|AAG|GTT|GAC|GTG|ATG|ATC|GAG|AAG|CAG|GGA|480|
|---|---|---|---|---|---|---|---|---|---|---|---|---|---|---|---|---|
|Asp|Arg|Val|Gly|Ser|Arg|Lys|Val|Asp|Val|Met|Ile|Glu|Lys|Gln|Gly| |
|145| | | | |150| | | | |155| | | | |160| |

|GGC|GGA|CGC|TCT|CCG|GAC|GCC|GAG|GGA|TTC|GGC|GTC|GTG|GGT|GGC|ATC|528|
|---|---|---|---|---|---|---|---|---|---|---|---|---|---|---|---|---|
|Gly|Gly|Arg|Ser|Pro|Asp|Ala|Glu|Gly|Phe|Gly|Val|Val|Gly|Gly|Ile| |
| | | | |165| | | | |170| | | | |175| | |

|CAC|GCC|AAG|GTG|AGC|CTA|GCC|GAG|AGG|GTC|TCG|GAC|GAC|ATA|CCC|GCC|576|
|---|---|---|---|---|---|---|---|---|---|---|---|---|---|---|---|---|

```
His Ala Lys Val Ser Leu Ala Glu Arg Val Ser Asp Asp Ile Pro Ala
            180                 185                 190

AGC AGG ATC ATG ATG GGC GAG GGT CTC CTC AGC GTG CTC TCC ACC CTC    624
Ser Arg Ile Met Met Gly Glu Gly Leu Leu Ser Val Leu Ser Thr Leu
        195                 200                 205

GAC GTC AAG TCG TTC CCT CCG CCC CAC GGC GAT TTG GTG AAC CGA GGC    672
Asp Val Lys Ser Phe Pro Pro Pro His Gly Asp Leu Val Asn Arg Gly
    210                 215                 220

GAG CTT GGC ACG CCC GAC CGG CCC TCG GAC AAG AGG AAT TAC ATT GAG    720
Glu Leu Gly Thr Pro Asp Arg Pro Ser Asp Lys Arg Asn Tyr Ile Glu
225                 230                 235                 240

GGA CAC GGG GAT TTC TCG GCC TGT TTC AGC TAC AAC CTG CGG ACC CCG    768
Gly His Gly Asp Phe Ser Ala Cys Phe Ser Tyr Asn Leu Arg Thr Pro
                245                 250                 255

CCG TCC AAC GCA ACA ACG CCC AGC GGA CGC CAC ATA TAC GTG AGC GCT    816
Pro Ser Asn Ala Thr Thr Pro Ser Gly Arg His Ile Tyr Val Ser Ala
            260                 265                 270

TCT CTG GTC AGG ACG ACG AGT TCA CCG ACT ACT TAG                    852
Ser Leu Val Arg Thr Thr Ser Ser Pro Thr Thr
        275                 280
```

( 2 ) INFORMATION FOR SEQ ID NO:4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

AACGGATCCG GAGGTTTAAA AATGAAGACG ATCGATCTAT TTTGC    45

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

CAAGGATCCT AACTGATCGC AACCTTTATT GTTTCA    36

( 2 ) INFORMATION FOR SEQ ID NO:6:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

AAGGGTGCTG AAGTACCCAA ACGCCGG    27

( 2 ) INFORMATION FOR SEQ ID NO:7:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear (i i) MOLECULE TYPE: cDNA (x i) SEQUENCE DESCRIPTION: SEQ ID NO:7:

GCGGAGAACA GCCGCCACAG ATGCGAC  27

(2) INFORMATION FOR SEQ ID NO:8:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:8:

TCGGGAAGCT GGGACCTTGC GAGC  24

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:9:

ACCACCTATA TCGCCACCGC ACCT  24

(2) INFORMATION FOR SEQ ID NO:10:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:10:

CTTCCCGACC ATATGGGGCC ATCAACGCTG AAAAGGAGA  39

(2) INFORMATION FOR SEQ ID NO:11:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:11:

GCTGGATCCT CAGCGAGGAT ATTTGCAGAC ACCATA  36

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: cDNA (x i) SEQUENCE DESCRIPTION: SEQ ID NO:12:

AACTCGTCGT CCTGACCAGA GAAG     24

(2) INFORMATION FOR SEQ ID NO:13:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

CGACTACTTA GTCGCCCAAC TGGC     24

(2) INFORMATION FOR SEQ ID NO:14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

TAATTCCTCT TGTCCGAGGG CCGG     24

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

ATTGAGGGAC ACGGGATTT CTCG     24

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:16:

CCCATGTCGG GCCAGCACTG GATT     24

(2) INFORMATION FOR SEQ ID NO:17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

ACTAGGTTGA CCGCCTTATT CAAG     24

(2) INFORMATION FOR SEQ ID NO:18:

(  i  ) SEQUENCE CHARACTERISTICS:
( A ) LENGTH: 24 base pairs
( B ) TYPE: nucleic acid
( C ) STRANDEDNESS: single
( D ) TOPOLOGY: linear (  i i  ) MOLECULE TYPE: cDNA ( x i ) SEQUENCE DESCRIPTION: SEQ ID NO:18:

CCCATGTCGG GCCAGCACTG GATT 24

( 2 ) INFORMATION FOR SEQ ID NO:19:

(  i  ) SEQUENCE CHARACTERISTICS:
( A ) LENGTH: 24 base pairs
( B ) TYPE: nucleic acid
( C ) STRANDEDNESS: single
( D ) TOPOLOGY: linear (  i i  ) MOLECULE TYPE: cDNA ( x i ) SEQUENCE DESCRIPTION: SEQ ID NO:19:

ATCAGGTTGA CCGCCTTATT CAAG 24

( 2 ) INFORMATION FOR SEQ ID NO:20:

(  i  ) SEQUENCE CHARACTERISTICS:
( A ) LENGTH: 24 base pairs
( B ) TYPE: nucleic acid
( C ) STRANDEDNESS: single
( D ) TOPOLOGY: linear (  i i  ) MOLECULE TYPE: cDNA ( x i ) SEQUENCE DESCRIPTION: SEQ ID NO:20:

AACTCGTCGT CCTGACCAGA GAAG 24

( 2 ) INFORMATION FOR SEQ ID NO:21:

(  i  ) SEQUENCE CHARACTERISTICS:
( A ) LENGTH: 24 base pairs
( B ) TYPE: nucleic acid
( C ) STRANDEDNESS: single
( D ) TOPOLOGY: linear (  i i  ) MOLECULE TYPE: cDNA ( x i ) SEQUENCE DESCRIPTION: SEQ ID NO:21:

TAATTCCTCT TGTCCGAGGG CCGG 24

( 2 ) INFORMATION FOR SEQ ID NO:22:

(  i  ) SEQUENCE CHARACTERISTICS:
( A ) LENGTH: 39 base pairs
( B ) TYPE: nucleic acid
( C ) STRANDEDNESS: single
( D ) TOPOLOGY: linear (  i i  ) MOLECULE TYPE: cDNA ( x i ) SEQUENCE DESCRIPTION: SEQ ID NO:22:

ATTTGCCCCC ATATGTGGTG TAATTATGAA GGCGGGGGA 39

( 2 ) INFORMATION FOR SEQ ID NO:23:

(  i  ) SEQUENCE CHARACTERISTICS:
( A ) LENGTH: 33 base pairs
( B ) TYPE: nucleic acid
( C ) STRANDEDNESS: single
( D ) TOPOLOGY: linear -continued (i i) MOLECULE TYPE: cDNA (x i) SEQUENCE DESCRIPTION: SEQ ID NO:23:

CGCGGATCCG AAACGCAGTC CCACCGTTGC TAG   33